United States Patent [19]

Khoury

[11] Patent Number: 5,151,096
[45] Date of Patent: Sep. 29, 1992

[54] LASER CATHETER DIFFUSER

[75] Inventor: Adib I. Khoury, Bellows Falls, Vt.

[73] Assignee: Angiolaz, Incorporated, Rockingham, Vt.

[21] Appl. No.: 676,307

[22] Filed: Mar. 28, 1991

[51] Int. Cl.⁵ ............................................. A61B 17/36
[52] U.S. Cl. ...................................... 606/15; 606/17; 606/7; 128/398
[58] Field of Search ............................ 606/7, 15–19; 128/397, 398

[56] References Cited

U.S. PATENT DOCUMENTS

| | | | |
|---|---|---|---|
| 4,660,925 | 4/1987 | McCaughan, Jr. | 606/15 X |
| 4,693,556 | 9/1987 | McCaughan, Jr. | 606/15 X |
| 4,819,632 | 4/1989 | Davies | 606/15 X |
| 4,860,743 | 8/1989 | Abela | 606/7 |
| 4,994,060 | 2/1991 | Rink et al. | 606/15 X |
| 4,998,930 | 3/1991 | Lundahl | 606/15 |

*Primary Examiner*—Peter A. Aschenbrenner
*Attorney, Agent, or Firm*—Malcolm J. Chisholm, Jr.

[57] ABSTRACT

A light transmitting and diffusing apparatus is disclosed for activating photodynamic therapy in soft cancerous tumors. In the preferred embodiment, the apparatus is affixed to a standard medical laser that transmits light through an optical fiber to a point adjacent to or within a cancerous tumor. The apparatus includes an unclad fiber-optic core with a reflective cap at a terminal end of the core. A diffuser matrix coats the unclad fiber-optic core and a transparent tubular sleeve encases the matrix and core. The transparent tubular sleeve includes a conical tip adjacent to the terminal end of the core for easy penetration of the cancerous tumors. In use, light leaves the medical laser, travels along the optical fiber into the unclad fiber-optic core. There, some light passes directly out of the core through the diffuser matrix, and the remaining light is reflected, by this reflective cap, back into and around the core, away from its terminal end. The resulting pattern of diffuse light is roughly shaped like a "butternut-squash", producing a decreased risk of damage to blood vessels, nerves, etc., that may be just beyond the terminal end of the core, along its longitudinal axis.

10 Claims, 2 Drawing Sheets

LASER CATHETER DIFFUSER

BACKGROUND OF THE INVENTION

The present invention relates to devices for transmitting and diffusing light energy at cancerous tumors to activate light sensitive drugs.

Various forms of cancer constitute the second leading cause of death in this country. For decades medical research has groped for a still elusive treatment that would cure cancer in its many forms or prevent its inception. Both government and private funds have enabled researchers to devolve more effective drug treatment regimens for certain cancers. Surgery, drugs, chemotherapy and radiation, individually or in combination, are preferred treatment procedures.

However, each of these approaches has some drawbacks. Surgical techniques cannot insure complete removal of malignant tumors, particularly those that have begun to metastasize. In their efforts to eradicate every vestige of cancerous growth, surgeons are often criticized for removing too much "good" tissue. Drugs have contraindications for their use, and individuals may exhibit different adverse reactions to them. Chemotherapy and radiation treatments often result in loss of appetite, weight and hair. Thus, while only certain portions of the body are treated, the whole body is often drastically affected.

To eliminate problems associated with such treatment procedures, innovative researchers designed what have come to be known as "magic bullet" treatment approaches. In such a treatment, a "magic bullet" is directed to a particular cancerous site within a body and exerts its effects only within that limited area. The body as a whole is not affected. Examples of such approaches are drug-filled, antibody-tagged red blood cell "ghosts" and drug-tagged monoclonal antibodies. Both the antibodies and red cell "ghosts" attach directly to tumor cells and release anti-carcinogenic drugs only at that site.

Another example of a "magic bullet" approach is photodynamic therapy (PDT). PDT relies on principles of photochemistry in which light of a specific wavelength and energy acts as a catalyst promoting certain chemical processes within a living cell. Common photochemical reactions encountered daily include those associated with vision and photosynthesis. Researchers used their knowledge of photochemical processes to devise the unique treatment therapy termed PDT.

In PDT, a patient is injected with a mixture of chemicals, for example, "hematoporphyrin derivative" ("HpD"). HpD is extracted from blood serum and is known to lodge preferentially within cancer cells. It remains within these cancer cells at a higher concentration than found in normal cells at 48-72 hours after injection. Subsequent exposure of drug-treated cells to light of specific energy level (chosen by a physician with respect to tumor nature and location) and wavelength (usually 630 nanometer, red light) results in death of the cancer cells without harm to surrounding normal, healthy tissue. While the specific reaction sequence leading to cell death is not fully understood, the phenomenon is well-known and increasingly used in cancer treatments. Patients must refrain from exposure to sunlight for several weeks after treatment since their sensitivity to light remains high during this time. No other side effects are known to accompany HpD treatment.

U.S. Pat. Nos. 4693556 and 4660925, both to McCaughan, describe devices for transmitting and diffusing light to various areas within the body. In these body areas, transmitted light energy activates photosensitive drug reactions (PDT). A tumor's location within the body dictates which of McCaughan's two inventions should be used for treatment. One version of the device has a spherical terminus for treating cavitary-area cancers like bladder tumors; the other version (shown in FIG. 5 of the present invention) has a cylindrical terminus with a flat distal end for treating tubular-area cancers such as esophageal cancers.

McCaughan's devices have inherent structural limitations in that neither one is able to penetrate and lodge within a tumor mass. Likewise, neither of these devices is appropriate for use where blood vessels or nerves, which may be adversely affected by intense light energy, traverse a tumor mass. Neither device has a shield to deflect light and thereby prevent destructive light energy from reaching beyond their light-emitting tips. A further limitation exists in the manufacture of McCaughan's light-dispersing devices. It requires a procedure involving successive layering of an epoxy-quartz mixture onto an optical fiber, which is costly in terms of both time and labor.

Accordingly, it is the general object of the present invention to provide an improved laser catheter diffuser that overcomes the problems of the prior art.

It is another object of this invention to provide an improved laser catheter diffuser capable of penetrating a malignant tumor mass, while simultaneously shielding certain areas within or adjacent to the tumor mass from harmful light radiation.

It is another object of this invention to provide a laser catheter diffuser that reflects and diffuses light to the greatest extent possible, thereby providing a maximum amount of light energy for activation of photochemical reactions in a drug activation cycle.

It is yet another object of this invention to provide a laser catheter diffuser that decreases time and cost factors associated with its manufacture.

The above and other objects and advantages of this invention will become more readily apparent when the following description is read in conjunction with the accompanying drawings.

SUMMARY OF THE INVENTION

An improved laser catheter diffuser apparatus is disclosed for transmitting and diffusing light energy within soft, cancerous tumors. A proximal end of the apparatus is attached to a standard medical laser. A distal end of the apparatus penetrates the tumor.

In the preferred embodiment, the invention comprises an unclad fiber-optic core with a reflective cap at a terminal end of the core. The unclad fiber-optic core extends from a fully clad fiber-optic laser catheter and is coated by a diffuser matrix. A transparent tubular sleeve encases the diffuser matrix coated fiber-optic core and reflective cap. The tubular sleeve includes a conical tip adjacent the terminal end of the core for easy penetration of the cancerous tumors.

In use, a medical endoscope is employed to position the laser catheter diffuser within a human body through direct visualization, in or along side a cancerous tumor mass. The medical laser at the proximal end of the laser catheter diffuser initiates a pulse of light. The light travels along the laser catheter and is reflected from side-to-side within the fiber-optic core by a cladding-layer surrounding the core. When the light reaches the unclad fiber-optic core, most of the light passes out of the core and diffuses away from the core by the diffuser matrix. Light that remains within the core reaches its terminal end and is reflected back by the reflective cap to diffuse out of the core via the diffuser matrix.

A cloud of diffused light energy surrounds the unclad fiber-optic core. The cloud is approximately the shape of a "butter-nut squash" or a butterfly rotated about a longitudinal axis of the core, wherein a bulge in the cloud protrudes away from the core, near its terminal end, as a result of the light reflected by the reflective cap. Light energy within the cloud is sufficient to activate photochemical reactions resulting in tumor cell death.

DETAILED DESCRIPTION OF THE PREFERRED EMBODIMENT

Figure 2:
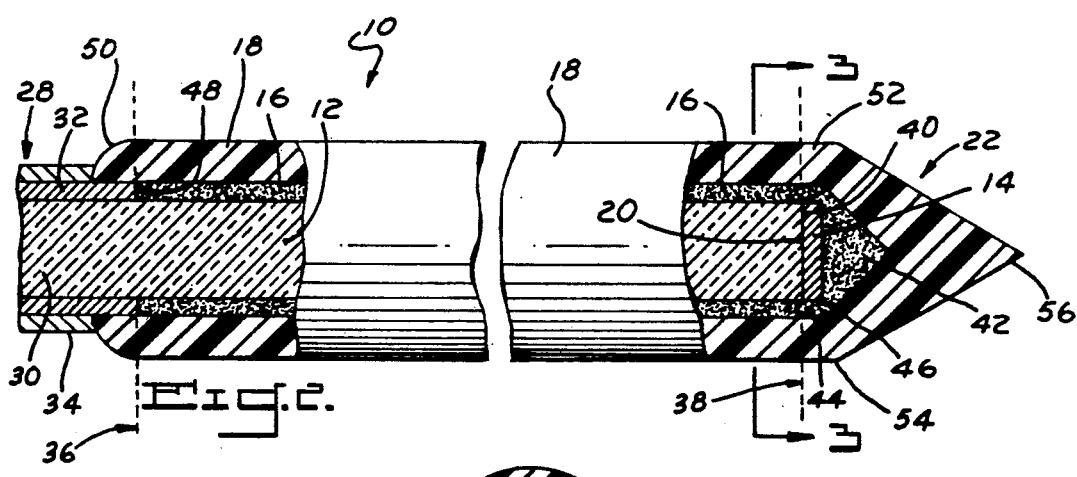
FIG. 2 is a cross-sectional view of the laser catheter diffuser taken along line 2—2 of FIG. 1.
Figure 3:
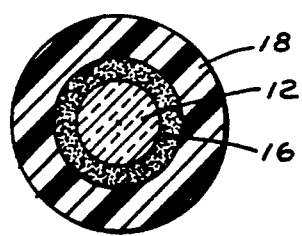
FIG. 3 is a cross-sectional view of the laser catheter diffuser taken along line 3—3 of FIG. 2.
Figure 4:
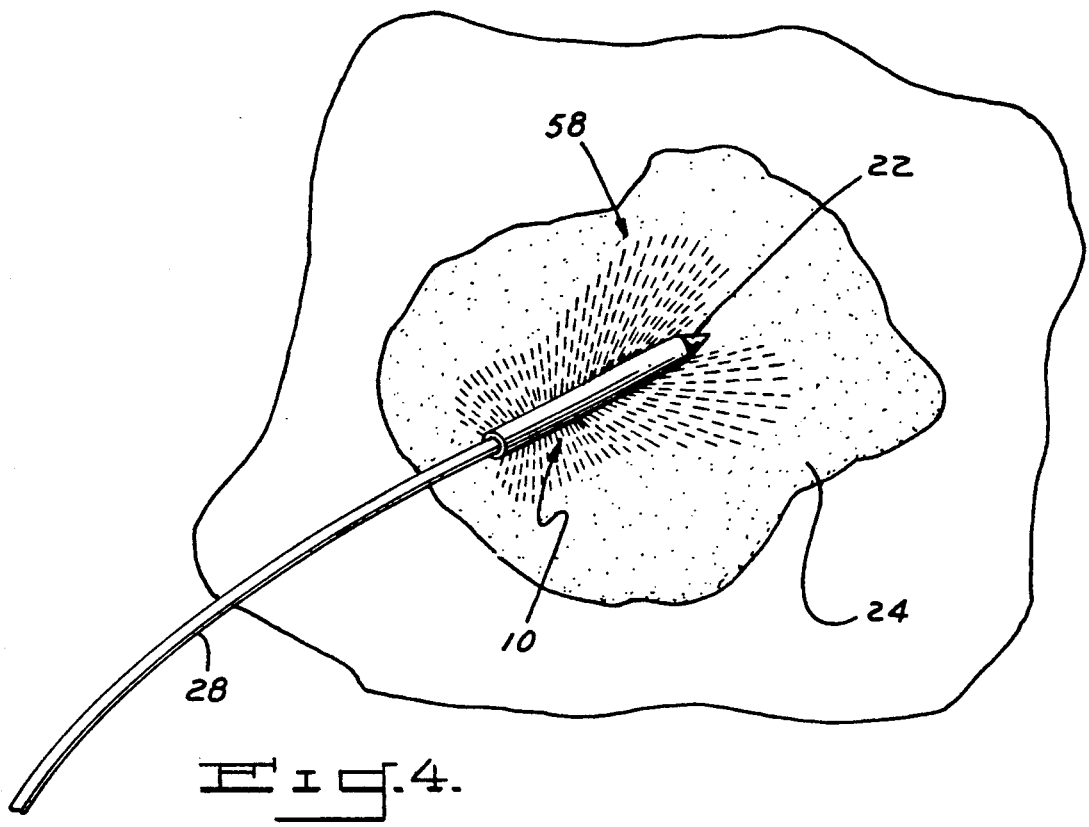
FIG. 4 is a schematic representation of a soft tumor mass with the laser catheter diffuser in place and indicating, in oblique radiating broken lines, a "butterfly"-shaped pattern of diffuse light emitted by the laser catheter diffuser.
Figure 5:
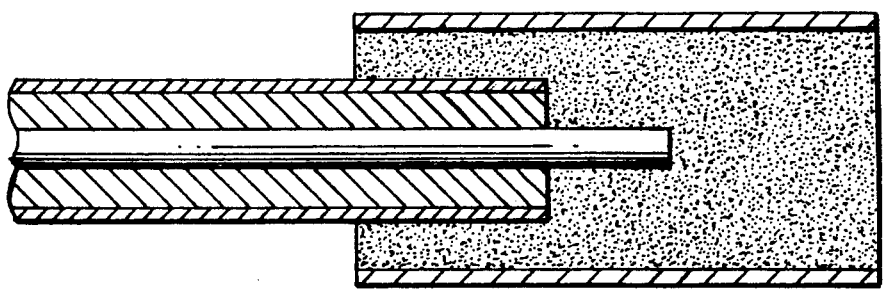
FIG. 5 is a cross-sectional view of a laser light-transmitting and diffusing device of the prior art.

Referring to the drawings in detail, the preferred embodiment of a laser catheter diffuser is shown and generally designated by the reference numeral 10. As best shown in FIGS. 2 and 3, the invention basically comprises an unclad fiber-optic core 12 having a reflective cap 14 at a terminal end 20 of the core that is adapted to reflect light traveling along the core back into the core; a glass-epoxy diffuser matrix 16 adjacent to and surrounding the unclad fiber-optic core 12 and reflective cap 14 to diffuse transmitted light as it radiates outward away from the core; and a transparent tubular sleeve 18 with an integral conical tip 22 to penetrate a tumor mass 24, as shown in FIG. 4.

Figure 1:
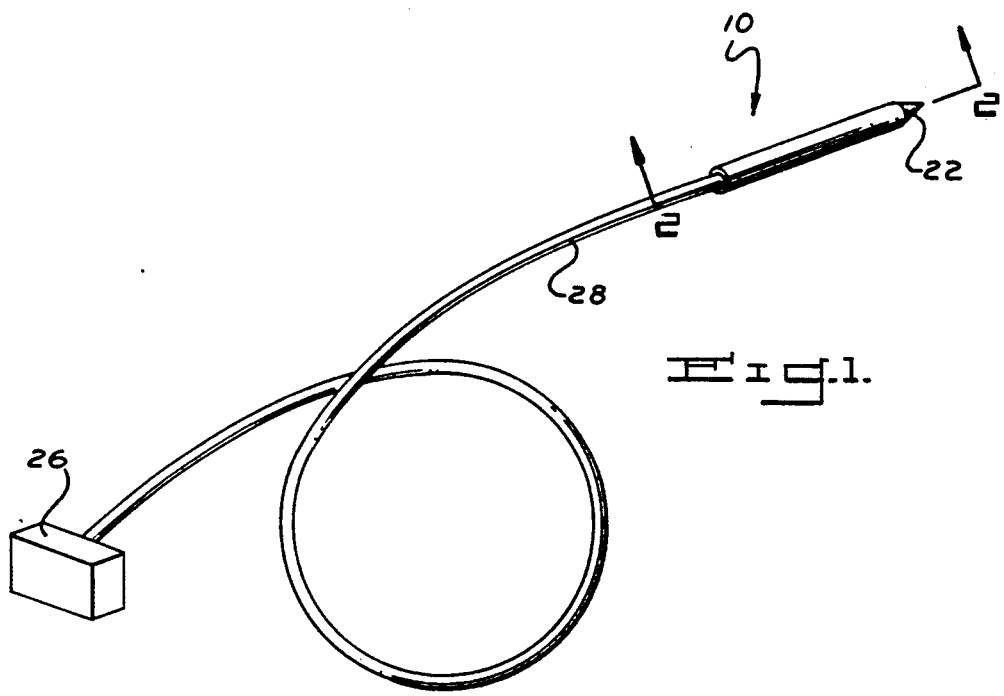
FIG. 1 is a perspective view of a laser catheter diffuser constructed in accordance with the present invention, wherein the diffuser is affixed to a standard medical laser.

As best shown in FIGS. 1 and 2, the laser catheter diffuser 10 includes a standard medical laser 26 such as a "P.D.T." medical laser manufactured by Meditec Aesculap of Haroldsburg, Federal Republic of Germany. The laser 26 is adapted to adjustably transmit laser light along a standard optical fiber or fiber optic 28 such as model "H.C.S." fiber optic, manufactured by Ensign-Bickford Optics Co. of Avon, Conn. As seen in FIG. 2, the optical fiber 28 includes a transparent fiber core 30 that is surrounded along its length by a cladding layer 32. The cladding layer is typically made of material that is similar to the transparent fiber core 30, but has a different reflective index, in order to enhance internal reflection of light passing through the core 30. An opaque exterior buffer layer 34 surrounds the cladding layer 32 along its length, to prohibit transmission of light out of the core 30 and protect it.

As shown in FIG. 1, the optical fiber 28 is of sufficient length to perform known procedures that employ medical lasers transmitting laser light along optical fibers. As best seen in FIG. 2, the optical fiber 28 is contiguous with the unclad fiber-optic core 12 at a point defined by a first unclad-core plane 36 that is perpendicular to a longitudinal axis of the optical fiber 28. The unclad fiber-optic core 12 extends from the first unclad-core plane 36 to a point defined by a second unclad-core plane 38 that is perpendicular to a longitudinal axis of the unclad fiber-optic core 12. The unclad fiber-optic core is formed by removing the cladding 32 and buffer 34 layers from a portion (not shown) of the optical fiber 28, by a standard removal process, such as sand blasting.

The reflective cap 14 is affixed to the terminal end 20 of the unclad fiber-optic core 12 at a point defined by the intersection of the second unclad-core plane 38 with a cross-sectional surface 40 of the unclad fiber-optic core 12. The reflective cap 14 is approximately disc-shaped and covers the entire surface 40, so that it caps the unclad fiber-optic core 12. In the preferred embodiment, the reflective cap 14 is comprised of standard silver paint such as "Ag/Agel Reflective Coating" manufactured by Ercon, Inc. of Waltham, Mass.

A pointed end 42 of the diffuser matrix 16 forms a collar 44 around an exterior edge 46 of the reflective cap 14. The collar 44 and exterior edge 46 are approximately parallel to the second unclad-core plane 38. The diffuser matrix 16 completely surrounds the unclad fiber-optic core 12, along its length, ending at an annular end 48 of the diffuser matrix 16. The annular surface end 48 surrounds the unclad fiber-optic core 12 and abuts the optical fiber 28 at a point adjacent to the first unclad-core plane 36. Standard medical grade epoxy (such as "Epo-Tek 301-2" manufactured by Epoxy Technology, Inc. of Billerica, Mass.) and medical grade glass beads, approximately 1–20 microns in diameter (such as "Dragonite Solid Glass Balls" manufactured by Jaygo, Inc. of Mahwah, N.J.) are mixed together in order to fabricate the diffuser matrix 16.

The transparent tubular sleeve 18 is affixed to and forms a housing around the diffuser matrix 16. A first circular edge 50 of the transparent tubular sleeve 18 surrounds the annular end 48 of the diffuser matrix 16 at a point approximately adjacent the first unclad-core plane 36. The sleeve 18 surrounds the diffuser matrix 16 and extends to a second circular edge 52 at a point adjacent to the second unclad-core plane 38.

The second circular edge 52 of the transparent tubular sleeve 18 is integral with an edge of widest circumference 54 of the conical tip 22. The tip includes a point 56 for shearing bodily tissue (not shown) so that the laser catheter diffuser 10 can penetrate tumor mass 24. Both the conical tip 22 and the transparent tubular sleeve 18 are fabricated from a single rigid material suitable to the purpose of the invention, such as "Lexan 154-111", namely, penetrating a tumor, manufactured and extruded by the General Electric Co., of Pittsfield, Mass.

The laser catheter diffuser 10 is formed by filling the transparent tubular sleeve 18 with the diffuser matrix 16 and then driving the unclad fiber-optic core 12, capped by the reflective cap 14, into the sleeve 18 so that the reflective cap 14 is adjacent the conical tip 22. The diffuser matrix 16 then hardens by standard curing to seal the laser catheter diffuser 10. In use, an operator (not shown) employs a standard medical endoscope (not shown) to locate a photochemically pre-treated tumor mass 24 targeted for destruction. The laser diffuser catheter 10 is guided into position alongside or within the tumor mass 24 to effect maximal tumor cell destruction. The conical tip 22 of the laser diffuser catheter 10 permits penetration of the tumor mass 24, if desired, for maximal tumor cell destruction.

Next, the operator actuates the medical laser 26 to deliver a pulse of laser light (not shown) to the optical fiber 28. The laser light travels along the optical fiber 28 and is contained within the fiber core 30 by the cladding 32 and buffer 34 layers exterior to the fiber core 30. As the laser light enters the unclad fiber-optic core 12, most of the light radiates outward through the diffuser matrix 16. Laser light is reflected and refracted by the diffuser matrix 16, and leaves the laser diffuser catheter 10 through the transparent tubular sleeve 18. Some laser light reaches the terminal end 20 of the unclad fiber-optic core 12 that is covered by the reflective cap 14. That laser light is reflected back into the unclad fiber-optic core 12 and leaves the laser diffuser catheter 10 through the diffuser matrix 16 and transparent tubular sleeve 18. The reflective cap 14 protects blood vessels, nerves and tissues beyond the conical tip 22 along or adjacent a longitudinal axis of the unclad fiber-optic core 12, by preventing destructive levels of laser light energy from exiting the laser diffuser catheter 10 in that area.

An overall pattern 58 of diffuse light in the shape of a butternut squash, or of a butterfly rotated about a longitudinal axis of the unclad fiber-optic core 12, emanates from the laser diffuser catheter 10 and defines the area of potential photochemical activation and tumor cell destruction.

It should be understood by those skilled in the art that obvious structural modifications can be made without departing from the spirit of the invention. For example, a laser catheter diffuser could be fabricated for special application, wherein the transparent tubular sleeve 18 is deleted and the diffuser matrix 16 is coated on to the unclad fiber-optic core 12. Accordingly, reference should be made primarily to the accompanying claims rather than the foregoing specification to determine the scope of the invention.

Having thus described the invention, what is claimed is:

1. An apparatus for transmitting light from a medical laser along an optical fiber to a cancerous tumor, that comprises:
   a. an unclad fiber-optic core extending from the optical fiber having any layers surrounding the fiber-optic core removed so that light travelling through the optical fiber and unclad fiber-optic core can pass out of the core;
   b. a reflective cap affixed to a terminal end of the unclad fiber-optic core so that light travelling through the optical fiber and unclad fiber-optic core is reflected by the reflective cap back into and around the unclad fiber-optic core away from the terminal end;
   c. a diffuser matrix that surrounds the unclad fiber-optic core and reflective cap so that light passing out of the core is diffused by the diffuser matrix; and
   d. rigid penetration means for penetrating the cancerous tumor, wherein the penetration means includes a transparent tubular sleeve that encases the diffuser matrix, unclad fiber-optic core and reflective cap so that light diffused by the diffuser matrix moves through the sleeve into the cancerous tumor.

2. The apparatus of claim 1 wherein the reflective cap comprises a reflective metallic paint.

3. The apparatus of claim 1 wherein the diffuser matrix comprises glass beads suspended within a medical grade epoxy.

4. An apparatus for transmitting light from a medical laser along an optical fiber to a cancerous tumor, that comprises:
   a. an unclad fiber-optic core extending from the optical fiber having any layers surrounding the fiber-optic core removed so that light travelling through the optical fiber and unclad fiber-optic core can pass out of the core;
   b. a reflective cap affixed to a terminal end of the unclad fiber-optic core so that light travelling through the optical fiber and unclad fiber-optic core is reflected by the reflective cap back into and around the unclad fiber-optic core away from the terminal end;
   c. a diffuser matrix that surrounds the unclad fiber-optic core and reflective cap so that light passing out of the core is diffused by the diffuser matrix;
   d. a transparent tubular sleeve that encases the diffuser matrix, unclad fiber-optic core and reflective cap so that light diffused by the diffuser matrix moves through the sleeve into the cancerous tumor; and
   e. a conical tip affixed to the transparent tubular sleeve and positioned so that the unclad fiber-optic core and conical tip share a common longitudinal axis and the conical tip extends beyond the reflective cap so that the conical tip shears an entry tunnel for penetration of the following transparent tubular sleeve, encased diffuser matrix, reflective cap and unclad fiber-optic core into the cancerous tumor.

5. The apparatus of claim 4 wherein the reflective cap comprises a reflective metallic paint.

6. The apparatus of claim 4 wherein the diffuser matrix comprises glass beads suspended within a medical grade epoxy.

7. The apparatus of claim 4 wherein the conical tip is adjacent to and surrounds the reflective cap.

8. An apparatus for transmitting light from a medical laser along an optical fiber to a cancerous tumor, that comprises:
   a. an unclad fiber-optic core extending from the optical fiber having any layers surrounding the fiber-optic core removed so that light travelling through the optical fiber and unclad fiber-optic core can pass out of the core;
   b. a reflective cap comprised of reflective silver paint wherein the reflective cap is affixed to a terminal end of the unclad fiber-optic core so that light travelling through the optical fiber and unclad fiber-optic core is reflected by the reflective cap back into and around the unclad fiber-optic core away from the terminal end;
   c. a diffuser matrix comprised of glass beads suspended within a medical grade epoxy wherein the diffuser matrix surrounds the unclad fiber-optic core and reflective cap so that light passing out of the core is diffused by the diffuser matrix;
   d. a transparent tubular sleeve that encases the diffuser matrix, unclad fiber-optic core and reflective cap so that light diffused by the diffuser matrix moves through the sleeve into the cancerous tumor; and e. a conical tip integrally affixed to the transparent tubular sleeve adjacent to and surrounding the reflective cap and positioned so that the unclad fiber-optic core and conical tip share a common longitudinal axis and the conical tip extends beyond the reflective cap so that the conical tip shears an entry tunnel for penetration of the following transparent tubular sleeve, encased diffuser matrix, reflective cap and unclad fiber-optic core into the cancerous tumor.

9. A method of manufacturing an apparatus for transmitting and diffusing light, said method comprising the steps of:

a. polishing an optical fiber to expose an unclad fiber-optic clad;

b. affixing a reflective cap to a terminal end of the unclad fiber-optical core;

c. filling a rigid transparent tubular sleeve with a diffuser matrix; and d. inserting the reflective capped unclad fiber-optic core into the diffuser matrix filled transparent sleeve so that the terminal end of the unclad fiber-optic core enters the transparent tubular sleeve first and the transparent tubular sleeve surrounds the unclad fiber-optic core.

10. The method of claim 9 wherein the step of affixing a reflective cap further comprises painting the terminal end of the unclad fiber-optic core with a reflective metallic paint.

* * * * *